United States Patent
Kupiecki et al.

(10) Patent No.: US 6,344,041 B1
(45) Date of Patent: Feb. 5, 2002

(54) ANEURYSM CLOSURE DEVICE ASSEMBLY

(76) Inventors: David Kupiecki, 10384 Alpine Dr. #3, Cupertino, CA (US) 95014; Clifford Teoh, 394 Alta Loma Ave., Daly City, CA (US) 94015; Hong Doan, 3765 Tamarack La. #59, Santa Clara, CA (US) 95051; Son M. Gia, 5065 Bengal Dr., San Jose, CA (US) 95111; Erik T. Engelson, 401 Encinal Ave., Menlo Park, CA (US) 94025; Uriel Hiram Chee, 127 Dolton Ave., San Carlos, CA (US) 94030; Mehran Bashiri, 3727 Village Ter. #277, Fremont, CA (US) 94536; Joseph C. Eder, 364 Marich Way, Los Altos, CA (US) 94022

( * ) Notice: Subject to any disclaimer, the term of this patent is extended or adjusted under 35 U.S.C. 154(b) by 0 days.

(21) Appl. No.: 09/699,267
(22) Filed: Oct. 26, 2001

Related U.S. Application Data

(63) Continuation of application No. 09/298,357, filed on Apr. 23, 1999, now Pat. No. 6,168,592, which is a continuation of application No. 08/690,183, filed on Jul. 26, 1996, now Pat. No. 5,980,514.

(51) Int. Cl.[7] ............................................. A61B 18/04
(52) U.S. Cl. .................... 606/32; 606/191; 606/198; 606/200; 604/104
(58) Field of Search ................... 606/32–42, 45–50, 606/108, 191, 196, 194, 198, 200, 95.05

(56) References Cited

U.S. PATENT DOCUMENTS

| | | |
|---|---|---|
| 4,512,338 A | 4/1985 | Balko et al. |
| 4,739,768 A | 4/1988 | Engelson |
| 4,878,906 A | 11/1989 | Lindemann et al. |

(List continued on next page.)

FOREIGN PATENT DOCUMENTS

| | | |
|---|---|---|
| EP | 0 547 530 A1 | 7/1991 |
| EP | 0 664 104 A2 | 7/1995 |
| EP | 0 820 726 A2 | 1/1998 |
| FR | 2 678 508 A1 | 7/1991 |
| JP | 4-47414 | 8/1990 |
| JP | 5-500322 | 1/1993 |
| JP | 6-54854 | 3/1994 |
| JP | 7-503165 | 4/1995 |

(List continued on next page.)

*Primary Examiner*—Linda C. M. Dvorak
*Assistant Examiner*—David Ruddy

(57) ABSTRACT

This is an artificial occlusion kit for implanting and retaining an artificial occlusion device in a body space adjacent to and extending from a body lumen in a mammal. The includes at least one occlusion device and a retaining device for blocking the migration of the occlusion device out of the occlusion site. The retaining device is radially expandable at a retaining site adjacent the body space to be occluded to a diameter that is sufficient to engage the body lumen wall at the retaining site and form a barrier across the entrance zone of the body space to be occluded. The expanded retaining device also forms a lumen for flow through body lumen at the retaining site. At least one semi-penetrable space may also be provided in the retaining device, allowing introduction of occlusion devices into the body space to be occluded, but preventing subsequent migration of the occlusion devices out of the body space. This semi-penetrable space may also be distensible to allow for delivery of occlusion devices therethrough. An introducer wire or a tapered-tip delivery catheter may be used to distend the distensible space and deliver the occlusion devices. The retaining device structure may further include a radiopaque metal wire wound into a primary helix over an inner core member made of a superelastic alloy of nickel and titanium. An implantable medical device assembly is also provided, having the structure described for the retaining device of the novel artificial occlusion kit, and which is attached to an elongate pusher via a sacrificial link that is electrolytically dissolvable.

11 Claims, 10 Drawing Sheets

U.S. PATENT DOCUMENTS

| | | |
|---|---|---|
| 4,994,069 A | 2/1991 | Ritchart et al. |
| 5,064,435 A | 11/1991 | Porter |
| 5,122,136 A | 6/1992 | Guglielmi et al. |
| 5,201,757 A | 4/1993 | Heyn et al. |
| 5,226,911 A | 7/1993 | Chee et al. |
| 5,250,071 A | 10/1993 | Palermo |
| 5,258,042 A | 11/1993 | Mehta |
| 5,261,916 A | 11/1993 | Engelson |
| 5,344,426 A | 9/1994 | Lau et al. |
| 5,344,444 A | 9/1994 | Glastra |
| 5,354,294 A | 10/1994 | Chou |
| 5,354,295 A | 10/1994 | Guglielmi et al. |
| 5,378,239 A | 1/1995 | Termin et al. |
| 5,389,106 A | 2/1995 | Tower |
| 5,397,355 A | 3/1995 | Marin et al. |
| 5,421,955 A | 6/1995 | Lau et al. |
| 5,423,885 A | 6/1995 | Williams |
| 5,443,496 A | 8/1995 | Schwartz et al. |
| 5,453,090 A | 9/1995 | Martinez et al. |
| 5,476,505 A | 12/1995 | Limon |
| 5,514,154 A | 5/1996 | Lau et al. |
| 5,522,836 A | 6/1996 | Palermo |
| 5,569,245 A | 10/1996 | Guglielmi et al. |
| 5,582,619 A | 12/1996 | Ken |
| 5,607,466 A | 3/1997 | Imbert et al. |
| 5,609,628 A | 3/1997 | Keranen |
| 5,639,277 A * | 6/1997 | Mariant et al. .............. 606/191 |
| 5,643,254 A | 7/1997 | Scheldrup et al. |
| 5,749,919 A | 5/1998 | Blanc |
| 5,795,331 A | 8/1998 | Cragg et al. |
| 5,951,599 A | 9/1999 | McCrory |
| 5,957,948 A | 9/1999 | Mariant |

FOREIGN PATENT DOCUMENTS

| | | |
|---|---|---|
| JP | 8-33715 | 2/1996 |
| JP | 8-187248 | 7/1996 |
| JP | 8-506512 | 7/1996 |
| WO | WO 91/13592 A | 9/1991 |
| WO | WO 95/25480 | 9/1995 |
| WO | WO 97/48351 | 12/1997 |

* cited by examiner

ANEURYSM CLOSURE DEVICE ASSEMBLY

CROSS-REFERENCE TO RELATED APPLICATIONS

This application is a continuation of U.S. patent application Ser. No. 09/298,357 filed Apr. 23, 1999, U.S. Pat. No. 6,168,592, which is a continuation of U.S. patent application Ser. No. 08/690,183 filed Jul. 26, 1996, U.S. Pat. No. 5,980,514.

FIELD OF THE INVENTION

This invention is an implantable medical device assembly for use in surgical procedures. The invention includes an artificial occlusion kit that uses a retaining device to prevent migration of artificial occlusion implants from an occlusion site, such as an aneurysm, and into an adjacent body space, such as a blood vessel.

BACKGROUND OF THE INVENTION

Different implantable medical devices have been developed for treating various ailments associated with body lumens, such as ailments of body vessel walls or other lumenal walls. One category of implantable medical device that has been developed for artificial occlusion of body spaces is the category of "artificial occlusion devices." Although artificial occlusion devices are useful in occluding body spaces, other applications include occluding body lumens. Examples of lumens that have been identified as candidates for treatment with artificial occlusion devices include, for example, the vas deferens or the fallopian tubes. Most commonly, however, artificial occlusion devices have been disclosed for medical treatment of the vascular lumens and aneurysms in the walls of such vessels. This treatment is commonly referred to as "artificial vaso-occlusion."

Artificial Vaso-occlusion

Artificial vaso-occlusion is a medical treatment that has involved techniques such as the delivery of various occlusive agents including solidifying suspensions, thrombogenic fluids, or emboli such as hog hair or suspensions of metal particles. Delivery of such agents or emboli normally causes a thrombogenic or other occlusive tissue response. Recent advancements in artificial occlusion of vessels and aneurysms have included the delivery and implantation of metal coils. Implantable metal coils that are useful as artificial occlusion devices in vascular lumens or aneurysms are herein referred to as "vaso-occlusion coils."

Vaso-occlusion coils generally are constructed of a wire, usually made of a metal or metal alloy, that is wound into a helix. Vaso-occlusion coils are normally delivered through microcatheters such as the type disclosed in U.S. Pat. No. 4,739,768 to Engelson. The microcatheter commonly tracks a guide wire to a point just proximal of or within the desired site for occlusion. The coil is advanced through the microcatheter and out the distal end hole so to at least partially fill the selected space and create an occlusion.

Once a vaso-occlusion coil is implanted at a desired site, occlusion results either from the space-filling mechanism inherent in the coil itself, or from a cellular response to the coil such as a thrombus formation, or both. The space-filling mechanism of the vaso-occlusion coil may be either based upon a pre-determined secondary geometry, or may be based upon random flow characteristics of the coil as it is expelled from a delivery sheath lumen.

Vaso-occlusion coils have been disclosed that have a secondary geometry or shape which dictates at least in part their space-filling occlusion mechanism. Such a secondary shape may include a secondary helical structure which involves the primary coil helix being itself wound into a second helix. In addition to the space-filling feature, another benefit to having a secondary coil shape is that it may allow the coil readily to anchor itself against the walls of a delivery site. For example, a vaso-occlusion coil having a secondary shape may be ejected from a sheath lumen where it was constrained in a stretched condition to have a first outer diameter equal to the sheath lumen inner diameter. When ejected, the coil passively expands to its secondary shape, often having a larger, second outer diameter to aid in space-filling the body cavity or lumen. This may be an expansion to the coil's relaxed, unrestrained memory state—or at least until the coil encounters a vessel wall against which it exerts a force to complete the anchoring process.

One example of a type of vaso-occlusion coil having a predetermined secondary shape is described in U.S. Pat. No. 4,994,069 to Ritchart et al. Ritchart describes a vaso-occlusive wire having a memory imparted thereto by heating the wire at about 800° F. for 24 hours after it is shaped. This memory is effective to return the wire from a stretched, linear condition in which it is advanced through a catheter to a space-filling relaxed condition as the wire is released from the catheter. The diameter of the secondary shape is approximately equal to and may be larger than the vessel in which it is deployed.

In contrast to vaso-occlusion coils having pre-determined secondary shapes that dictate in part their space-filling mechanism, other vaso-occlusion coils have been disclosed that take on random shapes when expelled from a delivery sheath. This type of vaso-occlusive coil is often referred to as the "liquid coil." One example of such a vaso-occlusive coil which takes on a random occlusive shape when delivered into a body space is disclosed in pending U.S. patent application Ser. No. 08/413,970, filed Mar. 30, 1995. This document describes very soft and flexible coils which are flow-injectable through the delivery catheter using, e.g., saline solution.

In addition to the various types of space-filling mechanisms and geometries of vaso-occlusion coils, other particularized features of coil designs, such as mechanisms for delivering vaso-occlusion coils through delivery catheters and implanting them in a desired occlusion site, have also been described. Examples of categories of vaso-occlusion coils based upon their delivery mechanisms include pushable coils, mechanically detachable coils, and electrolytically detachable coils.

One example of the type of vaso-occlusion coil referred to as the "pushable coil" is disclosed in U.S. Pat. No. 4,994,069 to Ritchart et al., introduced above. Pushable coils are commonly provided in a cartridge and are pushed or "plunged" from the cartridge into a delivery catheter lumen. A pusher rod advances the pushable coil through and out of the delivery catheter lumen and into the site for occlusion.

In contrast to pushable coils, mechanically detachable vaso-occlusion coils are integrated with a pusher rod and mechanically detached from the pusher after exiting a delivery catheter. Examples of such mechanically detachable vaso-occlusion coils are provided in U.S. Pat. No. 5,261,916 to Engelson, or U.S. Pat. No. 5,250,071 to Palermo.

Further in contrast to the mechanically detachable type of vaso-occlusion coil, the electrolytically detachable type is also integrated with a pusher rod, but is detached from the pusher by applying a direct current that dissolves a sacrificial link between the pusher and the coil. Examples of such electrolytically detachable vaso-occlusion coils are disclosed in U.S. Pat. No. 5,122,136 to Guglielmi, et al, and U.S. Pat. No. 5,354,295 to Guglielmi, et al.

A further improvement upon the electrolytic detachment mechanisms just previously referenced is disclosed in pending U.S. patent application Ser. No. 08/205,512, filed Mar. 3, 1994. This document describes superimposing an alternating current signal over the direct current signal, wherein a sensing circuit monitors the alternating current signal as an indicator of the progression of coil detachment. Improvements for enhancing the thrombogenic or other occlusive tissue response to metal coils have also been disclosed. For example, vaso-occlusion coils having vaso-occlusive fibers attached thereto have been described (see for example, U.S. Pat. No. 5,226,911 to Chee et al.). A further type of vaso-occlusion coil is used as a detachable dielectric electrode in a radio-frequency artificial vaso-occlusion system, as disclosed in pending U.S. patent application Ser. No. 08/497,507, filed Jun. 30, 1995.

The disclosures of the various patent and pending patent application documents identified in the preceding paragraphs are herein incorporated in their entirety by reference.

Vaso-occlusion Coils in Aneurysms

A wide variety of clinical abnormalities in body lumens may be treated with artificial occlusion methods. For example, artificial occlusion methods have been disclosed for treating feeder vessels into tumors, arterio-venous malformations, fistulas, and aneurysms of vessel walls. Among arterial abnormalities, aneurysms present particular medical risk due to the dangers of potential rupture of the thinned wall inherent in an aneurysm. Occlusion of aneurysms with vaso-occlusion coils without occluding the adjacent artery is a desirable method of reducing such risk.

In one disclosed method of treating aneurysms with vaso-occlusion coils, a microcatheter is initially steered into or adjacent the entrance of an aneurysm, aided by a steerable wire. The wire is then withdrawn from the microcatheter lumen and replaced by the vaso-occlusion coil. The vaso-occlusion coil is advanced through and out of the microcatheter, desirably being completely delivered into the aneurysm. After or during delivery of such a coil into the aneurysm, a portion of the coil might then migrate out of the aneurysm entrance zone and into the feeding vessel. This may cause an undesirable response of occluding the feeding vessel. Also, there is an additional risk that the blood flow may induce movement of the coil farther out of the aneurysm, resulting in a more developed embolus in the good vessel.

One type of aneurysm, commonly referred to as a "wide-neck aneurysm," is known to present particular difficulty in placing and retaining vaso-occlusion coils. Wide-neck aneurysms are herein referred to as aneurysms of vessel walls having a neck or "entrance zone" from the adjacent vessel, which entrance zone has a diameter that either: (1) is at least 80% of the largest diameter of the aneurysm; or (2) is clinically observed to be too wide to effectively retain vaso-occlusion coils that are deployed using conventional techniques.

In attempting to prevent potential migration of vaso-occlusion coils from aneurysms, catheter distal tip shapes may be formed on delivery microcatheters to help support the distal tip during deployment of vaso-occlusive agents. However, this may provide only a partial solution, particularly in the case of wide-neck aneurysms.

There is a need for a retaining device that is adapted to block an entrance zone to an aneurysm such that occlusion devices may be implanted in and retained within the aneurysm and are prevented from migrating through the entrance zone of the aneurysm and into the adjacent vessel.

SUMMARY OF THE INVENTION

This invention is a novel artificial occlusion kit, which includes a novel implantable medical device useful for retaining occlusion devices at an occlusion site, and related method for use. A particularly useful application of the invention is in the treatment of wide-neck aneurysms and aneurysms emanating from a curving vessel.

An artificial occlusion kit is provided for implanting and retaining an artificial occlusion device in a body space adjacent to and extending from a body lumen in a mammal. The artificial occlusion kit has at least one occlusion device adapted for filling at least a portion of the body space, and a retaining device assembly that includes a retaining device.

The retaining device of the artificial occlusion kit is adapted to be delivered and implanted at a retaining site in the body lumen adjacent to the body space to be occluded. This retaining device has a first shape that is radially expandable to a diameter that is sufficient to engage the wall of the body lumen at a retaining site adjacent the body space to be occluded. When engaged with the body lumen wall, the retaining device forms a lumen having a diameter that is sufficient to allow flow therethrough, and also forms a barrier that prevents occlusion devices that are implanted in the body space from migrating out of the body space and into the adjacent body lumen.

In one retaining device variation, the first shape is formed when the retaining device is radially constrained during delivery to the retaining site, and a second shape with an expanded outer diameter is formed when the retaining device is released from radial constraint at the retaining site. Either a coaxial delivery sheath or a coaxial delivery wire may provide this radial constraint. Alternatively, the retaining device may be balloon expandable from the first shape to the second shape.

In another retaining device variation, at least one semi-penetrable space is provided in the barrier formed at the entrance zone into the body space to be occluded. This retaining device may be delivered to the retaining site, followed by introduction of at least one occlusion device into the body space to be occluded through the semi-penetrable space.

In another aspect of the invention, the retaining device may be a metal wire wound into a primary helix that has a secondary geometry which is also a secondary helix. The adjacent windings of the secondary helix may be the semi-penetrable space provided by the appropriate retaining device variation.

In another variation, the semi-penetrable space is sized to allow at least one occlusion device, when radially artificially constrained to a first occlusion device outer diameter, to be inserted therethrough. Subsequent release of the radial constraint on the occlusion device allows it to reconfigure to a second outer diameter which prevents migration back through the semi-penetrable space.

In still a further variation, the semi-penetrable space of the retaining device is distendable. A delivery catheter with a tapered tip may be provided such that the semi-penetrable space is distendable by forcing the delivery catheter tip therethrough and into the body space to be occluded. Alternatively to a tapered-tip delivery catheter, an introducer wire is provided to distend the semi-penetrable spaces of the retaining device. At least one occlusion device is introduced into the body space to be occluded either coaxially through the delivery catheter or over the introducer wire. Subsequent withdrawal of the delivery catheter or introducer wire allows the once distended semi-penetrable space to reform to its original shape, forming a barrier against migration of the occlusion devices out of the occlusion site and into the adjacent lumen.

In a further variation of the artificial occlusion kit, the retaining device is a wire wound into a primary helix over a core member. In a preferred variation of this embodiment, the core member is a metal, preferably a shape-memory alloy, and most preferably a shape-memory alloy of nickel and titanium. The wire is also preferably a metal, most preferably radiopaque.

Each of the variations discussed herein may further include a smaller diameter "leading helix" in the retaining device to assist in the alignment and deployment of the retaining device as it exits the catheter.

An implantable medical device assembly is also provided, having the structure described for the retaining device of the novel artificial occlusion kit and which is attached to an elongate pusher via a sacrificial link that is electrolytically dissolvable. In one variation, this implantable medical device may take the form of the "wire wound over core member" variation described for the artificial vaso-occlusion kit aspect of the invention.

This invention includes methods for using the apparatus here described.

DETAILED DESCRIPTION OF THE INVENTION

The present invention provides a novel solution to the problem of vaso-occlusion device migration out of aneurysms or other implantation sites and into the feeding vessels that are not the target of vaso-occlusion. A retaining device is used in a novel artificial occlusion assembly to prevent migration of one or more occlusion devices from a target occlusion site by forming a barrier at the entrance zone to the target site from a feeding vessel. Variations of a novel implantable medical device are provided as the retaining device, which novel implantable medical device is included within the scope of the present invention.

Artificial Occlusion Kit w/ Retaining Device

Figure 1A:
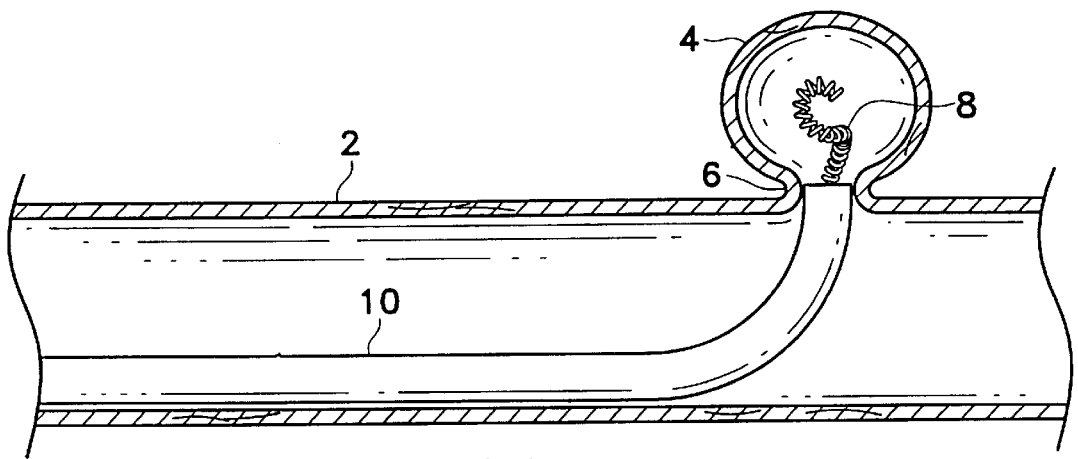
FIG. 1A shows a side view of a vessel with an aneurysm in its wall, wherein a vaso-occlusion coil component of an artificial occlusion kit is shown being delivered into the aneurysm.
Figure 1B:
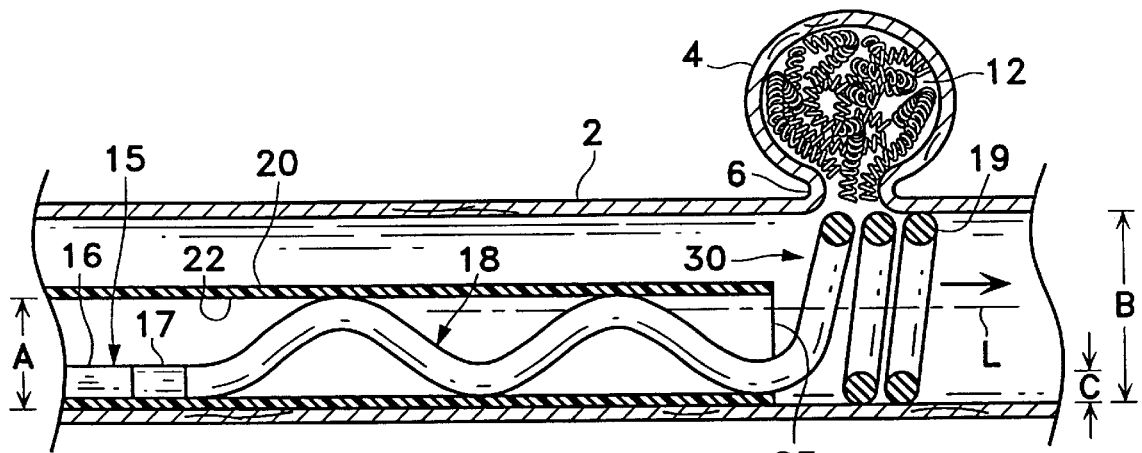
FIG. 1B shows a side view of the vessel and aneurysm of FIG. 1A, wherein a retaining device assembly of the artificial occlusion kit is shown being delivered to a retaining site in the vessel adjacent the aneurysm which is substantially filled with a plurality of vaso-occlusion coils.
Figure 1C:
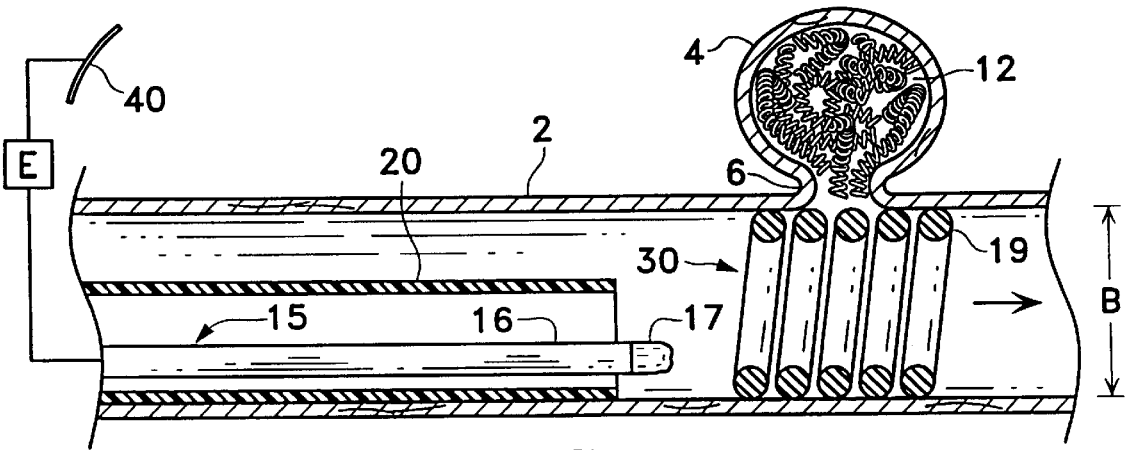
FIG. 1C shows a side view of the same vessel and aneurysm wherein the retaining device is shown electrolytically detached from a pusher, the retaining device engaging the vessel wall adjacent the entrance zone of the aneurysm, bridging across the entrance zone to form a barrier against vaso-occlusion coil migration into the vessel, and forming a lumen allowing for physiological flow through the vessel.

FIGS. 1A–C show sequential steps of a novel method of occluding a body space—here an aneurysm of a body lumen wall—using one artificial occlusion kit embodiment of the current invention. In this series of Figures, a retaining device is provided in a kit together with at least one vaso-occlusion device, which kit is also shown in use with at least one delivery catheter.

FIG. 1A shows the first of a plurality of vaso-occlusion coils is shown as it is being implanted into an aneurysm. In FIG. 1B, a retaining device of a retaining device assembly is shown being delivered to a retaining site in the body lumen adjacent the aneurysm after the aneurysm is substantially occluded with vaso-occlusion coils. In FIG. 1C, the retaining device is completely implanted at the retaining site and detached from a pusher via electrolytic detachment from a pusher. The implanted retaining device shown forms a barrier against migration of the vaso-occlusion coils from the aneurysm and into the body lumen, while maintaining an open conduit for flow through the body lumen.

In FIG. 1A, a cut-away side view of a vessel (2) having an aneurysm (4) in its wall is shown. Vaso-occlusion coil (8) is shown being delivered into aneurysm (4) out of the distal end of delivery catheter (10) in order to occlude the aneurysm (4).

Vaso-occlusion coil (8) for the purposes of this invention may be any one of a wide variety of coils that are known in the art for occluding vessels or aneurysms. For example, vaso-occlusion coil (8) may be a pushable coil of the type described in U.S. Pat. No. 4,994,069. Or, coil (8) may be a mechanically detachable coil such as that described in U.S. Pat. No. 5,261,916 or U.S. Pat. No. 5,250,071. Alternatively, coil (8) may be an electrolytically detachable coil such as that described in U.S. Pat. No. 5,122,136 or U.S. Pat. No. 5,354,294.

Still further, vaso-occlusion coil (8) may have a preformed secondary shape that is constrained in a stretched orientation when being delivered through delivery catheter (10) but reconfigures when delivered beyond delivery catheter (10). Such reconfiguring often includes radial expansion to a relaxed memory state having a desired, pre-determined shaped geometry. Alternatively, coil (8) may have highly flexible portions that ball up from random convolutions formed while the coil flows distally during delivery, such as the coils described in pending U.S. patent application Ser. No. 08/413,970, filed Mar. 30, 1995.

The type and geometry of vaso-occlusion coil are normally chosen for the particular delivery mechanism and space-filling characteristics, as may be appropriate for a particular occlusion site. The disclosures of the above referenced vaso-occlusion coil documents are herein incorporated by reference.

The appropriate design for delivery catheter (10) is defined by the ability to reach the desired occlusion site atraumatically and to efficaciously deliver the vaso-occlusion coil into the site as an occlusion implant. One example of a catheter that may be used in the present invention is described in U.S. Pat. No. Pat. 4,739,768 to Engelson, the disclosure of which is herein incorporated by reference.

FIG. 1B shows a retaining device (19) being delivered through delivery catheter (20) and into vessel (2) at the site of aneurysm (4). A plurality of vasoocclusion coils (12) is also shown having been implanted into aneurysm (4) prior to delivery of the retaining device (19). Retaining device (19) is shown as a distal segment of a retaining device assembly (15), wherein it is attached at its proximal end to a pusher (16) which is relatively more stiff than the implantable retaining device (19). Pusher (16) is adapted for advancing the retaining device percutaneously through the delivery catheter (20), even when in tortuous bends of the vasculature, into remote internal body spaces for occlusion.

In retaining device assembly (15), retaining device (19) and pusher (16) are shown to be coupled or attached via a joint or link (17). The scope of this invention contemplates that retaining device (19) and pusher (16) can be either electrolytically detachable at link (17) or mechanically detachable at link (17). In the electrolytically detachable embodiment, link (17) is electrolytically dissolvable when current is applied thereto. Electrolytic detachment mechanisms of the types described in U.S. Pat. No. 5,122,136 or U.S. Pat. No. 5,354,295 may be suitable. In the mechanically detachable embodiment, pusher (16) and retaining device (19) are mechanically detachably engaged at link (17). In such an assembly, the mechanical detachment mechanisms of the types described in U.S. Pat. No. 5,261,916 or U.S. Pat. No. 5,250,071 may be suitable. The disclosures of these above referenced electrolytically and mechanically detachable coil disclosures are herein incorporated by reference.

It is further contemplated that the use of a retaining device to prevent migration of vaso-occlusion devices from an occlusion site need not be limited to use with a "detachable" pusher-retaining device mechanism as is shown in retaining device assembly (15). It may be equally efficacious, and perhaps even preferred in a given circumstance, to use separate, non-attached retaining device and pusher without the need for a detachable link such as link (17).

Where the pusher is separate and not attached to the retaining device, pushers such as the type described in U.S. Pat. No. 4,994,069 to Ritchart et al. may be satisfactory. In use, the distal end of the pusher can be advanced axially within a delivery catheter lumen to abut a proximal end of the retaining device, also disposed within the delivery lumen. With the distal pusher end in confronting engagement with the retaining device proximal end, further advancement of the pusher by the user will effectively push the retaining device distally through the lumen, out of the delivery catheter from a distal port thereof, and into a vessel site adjacent a body space where occlusion devices are deployed.

In the artificial occlusion kit variation of FIG. 1B, retaining device (19) has a memory in the form of a pre-determined, shaped, secondary geometry. Retaining device (19) is shown to have a first shape with a first outer diameter "A" where it is positioned within delivery catheter (20). The delivery lumen (22), which ends distally in distal delivery port (23), radially constrains the retaining device such that the first outer diameter is defined by the delivery lumen (22) inner diameter. When released from a radially constraining condition, retaining device (19) also forms a second shape with a second outer diameter greater than the first outer diameter "A." and sufficient to engage the vessel wall. In FIG. 1B, retaining device (19) is shown extending beyond the distal delivery port of the delivery lumen (22) where it is radially artificially unconstrained and expanded to an outer diameter "B" larger than the first diameter "A," engaging the lumen wall at the retaining site adjacent the aneurysm.

It is contemplated that the completely relaxed, unconstrained second outer diameter of the retaining device may be slightly greater than the diameter of the vessel. This may be necessary in order to maintain accurate placement of the retaining device in the vessel lumen at the aneurysm site. However, the purpose of the retaining device is merely to form a barrier at the entrance zone of the aneurysm to prevent occlusion coil migration. Unnecessary trauma to the vessel wall, such as from oversizing or coil designs that are too stiff to perform the stated purpose should be avoided.

Retaining device (19) is shown in FIG. 1B to have a helical geometry. In one preferred embodiment, retaining device (19) is a metal wire that is wound into a primary helix, shown in FIG. 1B having a primary helix diameter "C". This primary helix is preferably pre-formed into a secondary geometry that, as shown for this embodiment, is also in the form of a secondary helix. Therefore, the first and second shapes and corresponding first and second outer diameters that the retaining device takes when being delivered to and implanted in the vessel, respectively, are defined by the secondary geometry of the retaining device. These shapes are formed about a longitudinal axis, shown in FIG. 1B at "L," and their respective outer diameters are defined on a radial plane perpendicular to that axis.

Retaining device (19) is also shown in FIG. 1B to form a lumen (30). In this embodiment, lumen (30) is defined by the simple helical shape of the retaining device's secondary geometry and extends along the longitudinal axis "L" of that helix. It is contemplated that first and second shapes other than a simple helix may still fall within the scope of the present invention. However, the purpose of the retaining device is to form a barrier at the entrance zone to the body space being artificially occluded by occlusion devices. Occlusion of the body lumen adjacent to the occlusion site is to be avoided in the use of the present invention. It is therefore an important aspect of the present invention that there be a physiologically acceptable through-lumen formed by the retaining device when implanted into the body lumen.

In the artificial occlusion kit embodiment of FIG. 1B, delivery catheter (10) may be the same catheter as that used for delivering the occlusion devices, such as delivery catheter (10) in FIG. 1A. Or, the two delivery catheters may in certain circumstances have different required characteristics for delivering the occlusion devices and retaining devices, respectively. For instance, a desired tip shape for delivering the occlusion devices into an aneurysm radially at the vessel wall may be different than the tip shape appropriate for delivering the retaining device transversely into the vessel lumen adjacent the aneurysm. Similarly, the retaining device and the occluding devices are characteristically of different designs, since one's function is to substantially space fill and the other's is to form a barrier at the aneurysm and also to keep the vessel lumen open. Thus, the delivery catheters for the two designs may require different delivery lumen diameters, material construction, etc. as may be appropriate according to one of ordinary skill.

The current invention further contemplates radially expandable retaining device assemblies other than the type that is delivered through a radially confining sheath. For instance, a delivery wire may provide a coaxial rail over which a retaining device may be advanced such as by a pusher located proximally of the retaining device. In such an assembly, the retaining device may have a lumen that coaxially tracks the delivery wire, the delivery wire providing radial constraint on the retaining device to form the first radially constrained shape. Advancing the retaining device distally past the end of the delivery wire releases the radial constraint and allows the retaining device to expand to a second shape.

Alternatively, a further retaining device variation may be delivered upon and expanded by a balloon on the distal end of a balloon catheter. In such a variation, the retaining device is provided for delivery to the retaining site while it is formed in its first shape coaxially engaged over a balloon in a deflated state. Once at the retaining site, inflation of the balloon radially expands the retaining device into a second shape having an outer diameter sufficient to engage the vessel wall and which forms a barrier across the entrance zone to an aneurysm. Subsequent deflation and withdrawal of the balloon leaves the radially expanded retaining device implanted at the retaining site, which retaining device forms a lumen where the expanded balloon once was.

Electrolytically Detachable Retaining Device

In FIG. 1C, a particular retaining device variation is shown detached at the retaining site in vessel (2) that is adjacent to a body space to be occluded, here aneurysm (4). Retaining device (19) is shown having a shape that is expanded along its length to a diameter sufficient to engage the vessel wall at regions adjacent an entrance zone (6) to aneurysm (4). Retaining device (19) also bridges across entrance zone (6) and forms a barrier against any of the plurality of vaso-occlusion devices (12) from migrating out of the aneurysm and into vessel (2).

In the embodiment shown in FIG. 1C, retaining device (19) has been detached from pusher (16) by means of electrolytic or erosive severing of link (17). As mentioned earlier, such electrolytic detachment may occur via the systems and methods as described in U.S. Pat. No. 5,122,136; U.S. Pat. No. 5,354,294; or co-pending U.S. patent application Ser. No. 08/499,525, filed on Jul. 7, 1995, as may be apparent to one of ordinary skill in the art. The disclosures of these documents have previously been incorporated by reference. Much different from those disclosures, however, is the fact that the retaining device of the current invention is not an occlusion device and must provide a through-lumen for flow when implanted into a vessel lumen (in fact the opposite function of the previously disclosed electrolytically detachable occlusion devices).

Briefly, however, power source "E" is electrically coupled to electrolytically severable link (17). An electrode (40) is also shown schematically in FIG. 1C, where it is also shown electrically coupled with power source "E." Electrode (40) may be a skin electrode having a relatively high surface area in contact with the patient when compared to that of link (17).

In clinical use, retaining device assembly (15) is disposed within the body such that link (17) is in patient contact. Since electrode (40) is in skin contact with the patient, a circuit may be formed wherein direct current from power source "E" may pass through link (17), quickly dissipate at a low current density through the patient as an electrical conductor, and through electrode (40) back to power source "E." This current serves to dissolve link (17) until retaining device (19) is detached from pusher (16).

Power source "E" may additionally superimpose an alternating current over the direct current signal, which alternating current signal may be sensed by a sensing circuit (not shown) as an indicator of the progression of electrolytic detachment at link (17). Additionally, a control circuit (not shown) may be used to alter the output power signal or shut the signal off upon the sensing of a critical parameter by the sensing circuit, such as the sensing of a particular change in the alternating current component of the output signal. Such monitoring and feedback control of electrolytic detachment may employ the apparatus and methods as described in co-pending U.S. patent application Ser. No. 08/205,512 filed Mar. 3, 1994 (previously discussed).

In the artificial occlusion kit embodiments described, cross sectional intrusion into the vessel lumen where implanted should be kept to a minimum. Beneficially to this invention, the electrolytic detachment allows for minimal engaging structure at the detachable coupling end of the implantable medical device (as compared to mechanically detachable designs which may require clasps, enlarged balls, etc. on the end of the implant coil). It is believed, therefore, that electrolytic dissolution of link (17) thus provides an optimal solution for implanting an implantable medical device for use as an occlusion coil retaining device.

Figure 2A:
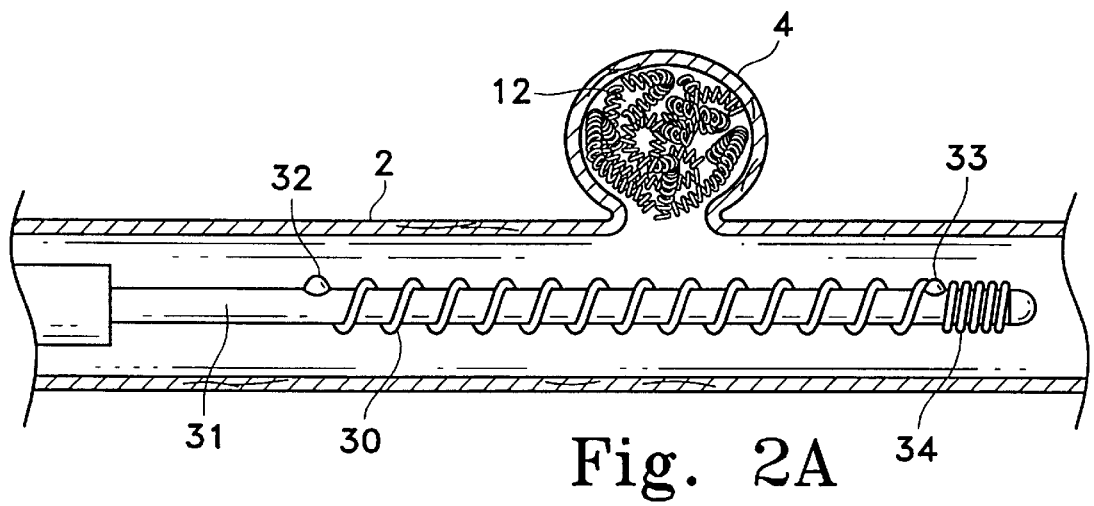
FIGS. 2A–2C show in partial section, a side view of an electrolytically deployed device.
Figure 2B:
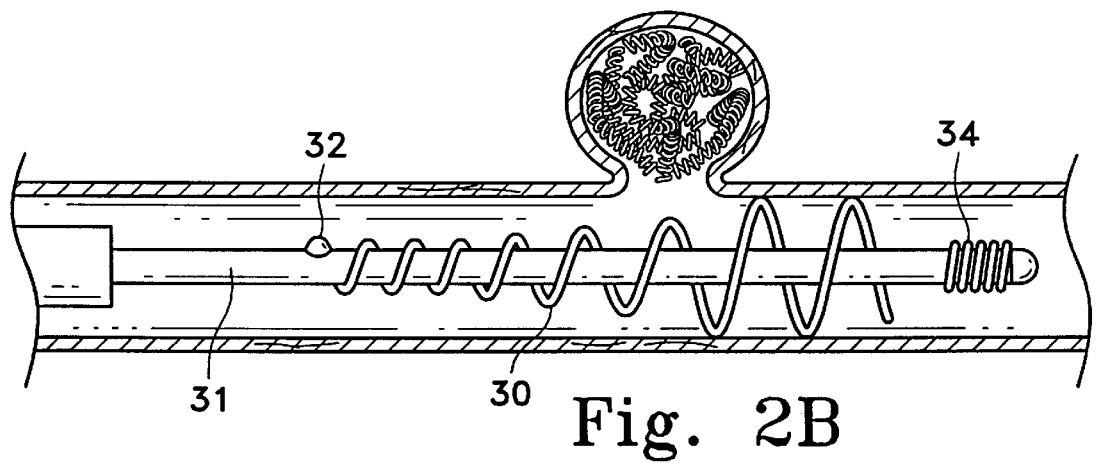
Figure 2C:
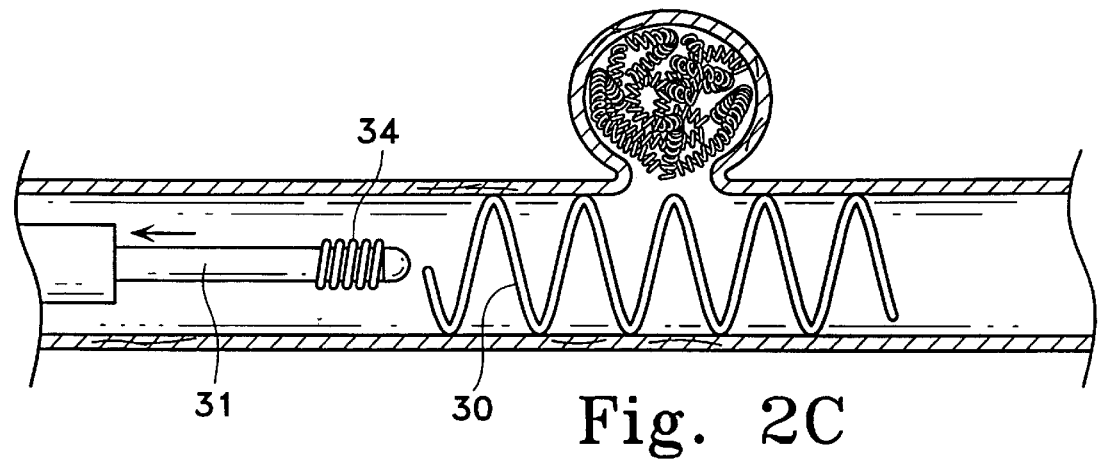

FIGS. 2A–2C depict a different variation of the artificial occlusion kit. In this variation, a vaso-occlusive coil (12) is maintained in an aneurysm (4) emanating from an artery (2) by a retaining device assembly (30) which is delivered to the site of the aneurysm (4) by guidewire. The retaining device assembly (30) is maintained in a radially compressed fashion by the use of a pair of electrolytic links (32, 33). As will be shown below in discussion of FIG. 3.

FIG. 2A shows the retaining device assembly (30) closely coiled to the body of the core or guidewire (31). Preferably, the retaining device assembly (30) is of a material or has been treated in such a way that the "normal" or relaxed condition of the retaining device assembly (30) is as shown in FIG. 2C. A single wire device is depicted in FIGS. 2A, 2B and 2C, but a helically wound coil is certainly suitable as well. In the variation shown in these figures, the retaining device assembly (30) must be either insulated in its entirety from the surrounding fluid (via, e.g., a plastic coating or the like) or of a material which is more noble or higher in the electromotive series than are the links (32) and (33) shown in the drawing. Further, the guidewire (31) distal tip coil (34) and the like must be insulated as well. As was discussed above in some detail, this detachment link operates via the electrolytic erosion of the bare links found at (32) and (33).

In the sequence shown in FIGS. 2A, 2B and 2C, the link found at (33) is smaller in diameter than is the link found at (32). In this way, as current is applied to core wire (31) and passes from that core wire into the links (32) and (33), link (33) erodes to a point where it breaks earlier than does the link at (32) simply because of the smaller diameter of link (33).

Once link (33) has disintegrated as is shown in FIG. 2B, link (32) continues to electrolytically erode as time passes. After the second joint (32) has broken and the retaining device assembly (30) has expanded as shown in FIG. 2C, the core wire and its allied parts (31) are removed.

Figure 3:
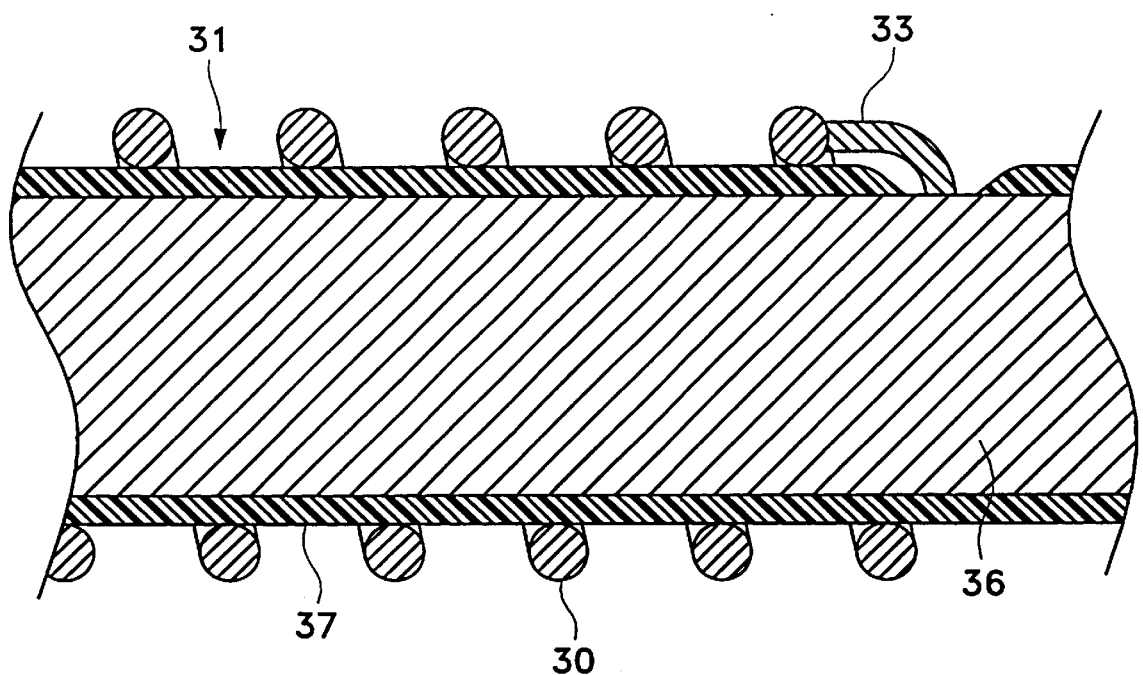
FIG. 3 shows in side view cross-section, a portion of the device shown in FIGS. 2A–2C emphasizing the section of the device employing an electrolytically erodible link.

FIG. 3 shows a portion of the core wire (31) with the retaining device assembly (30) closely disposed on its outer surface as would be the case in FIG. 2A. In this close up arrangement, the inner core (36) is covered by an insulating layer (37) of, e.g., a polytetrafluoroethylene. The displayed link (33) is in an electrical contact with the core (36) and holds the retaining device assembly (30) in close contact with the core wire assembly (31). It is this link (33) which erodes to release the retaining device assembly (30).

Figure 4A:
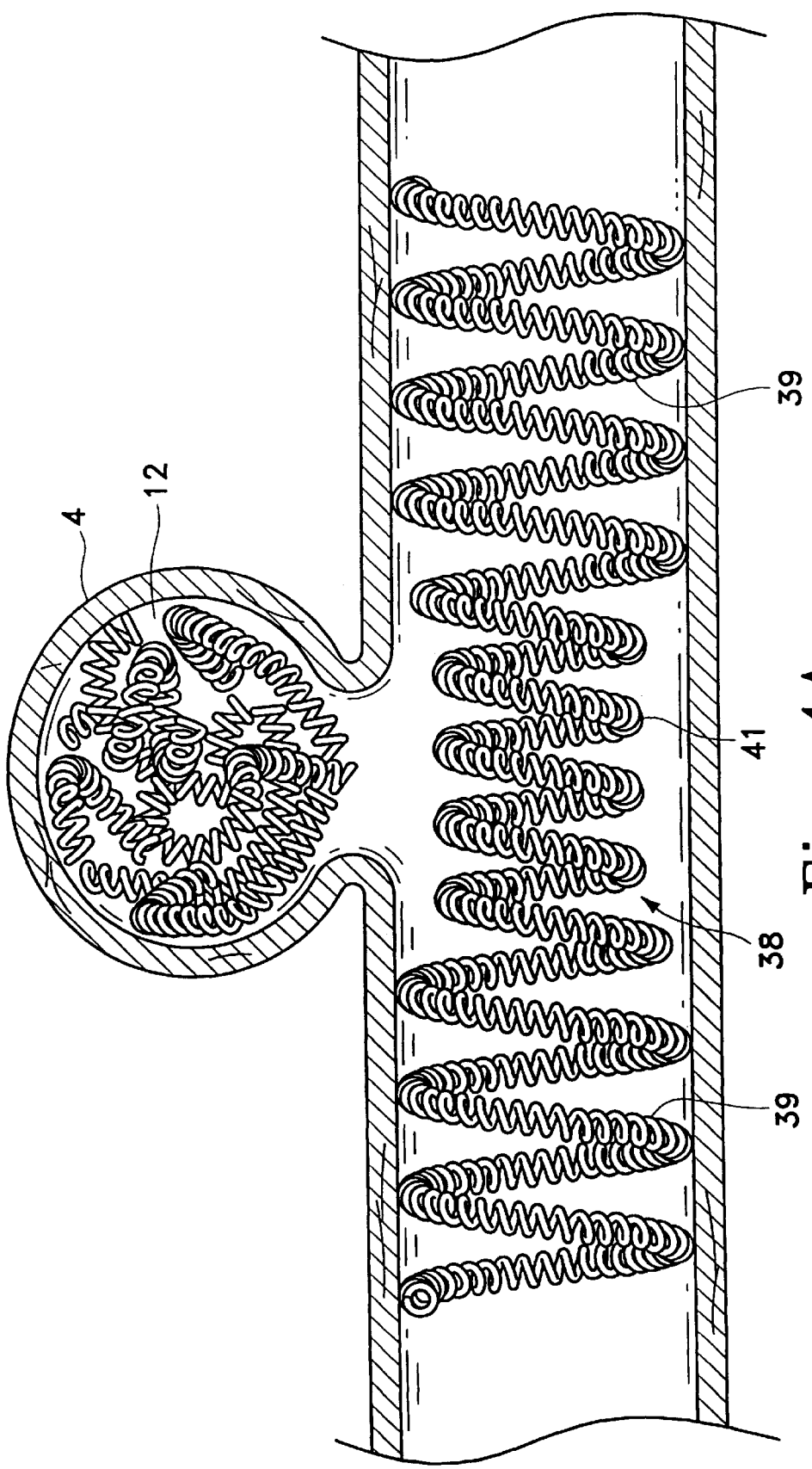
FIGS. 4A, 4B, and 4C show in partial cut-away, cross-section, variations of the shape of retainers made according to this invention.

FIG. 4A shows a variation of the overall shape of a retaining device assembly (38) made in keeping with this invention. In particular, the retaining device assembly (38) has two end regions (39) which have a diameter when deployed which approximates (or is slightly larger than) the inner diameter of the vessel lumen into which it is placed. The retaining device assembly (38) has a center section (41) which has a smaller overall radius than the two end sections (39). The smaller mid-section (41) has a variety of benefits. For instance, it does not press on the vessel or on the coil (12) within aneurysm (4). Yet it is sufficiently close to the mouth of aneurysm (4) to prevent coil (12) from migrating to other parts of the body. The retaining device assembly (38) made in this form is easier to move should it be mal-placed in the human body. It has smaller regions in contact with the vessel lumen.

The shape of the device is not particularly critical in many of these variations. The shape of retaining device assembly (38) must be sufficiently appropriate for it to maintain the coil (12) within aneurysm (14). It must have sufficient radial springiness to allow its shape to be maintained in the lumen of the body vessel described herein.

We have found that, on occasion, the retaining devices shown in the Figures will not achieve the desirable generally cylindrical shape found in those Figures. This problem can be alleviated in a variety of ways. A careful user will find it possible to twist the catheter during the initial ejection of a couple of turns of the retaining device assembly to maintain the device in the proper orientation in the lumen. Some users will find that the use of a catheter distal tip having a turn will help in deployment f the retainer. One very effective and highly desirable method of preventing the retainer from turning in the vessel lumen during deployment is found in FIGS. 4B and 4C. In this variation of the invention, the retaining device assembly (43 in FIG. 4B and 46 in FIG. 4C), incorporates a leading or distal helix section which has a deployed diameter which is smaller than the diameter of the vessel lumen.

Figure 4B:
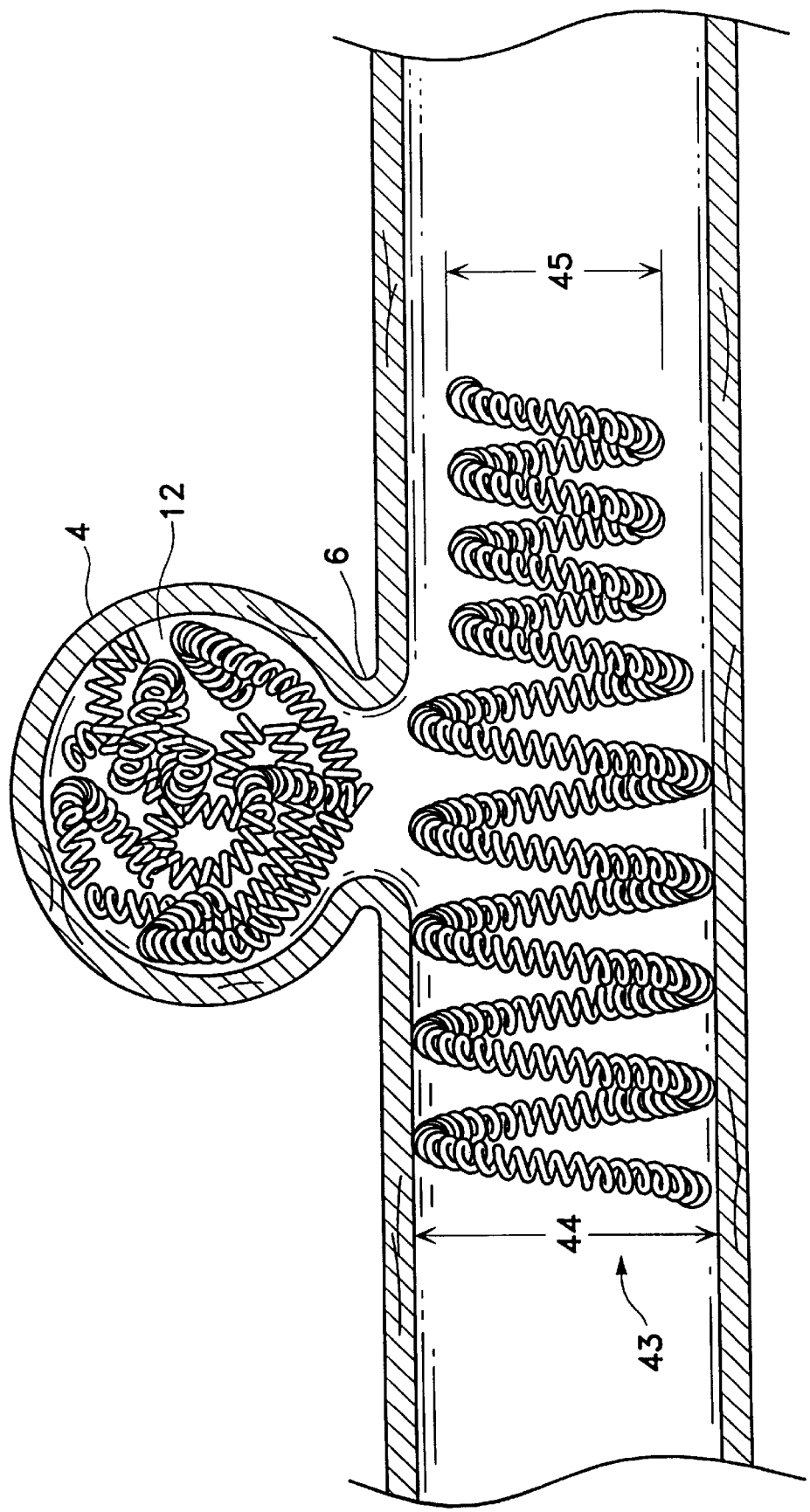

In FIG. 4B, the retaining device assembly (43) is first deployed to the right (or distal end) of the Figure. The proximal end of the retaining device assembly has a diameter (44) which is equal to or larger than the diameter of the vessel lumen. The earlier deployed distal end has a smaller diameter (45). During deployment of the device, the smaller diameter distal section exits the catheter end and simply forms a tubular cylinder within the lumen of the vessel. The distal end of the retainer device assembly (43) conceptually forms an indexing end and aligns the remainder of the retainer device assembly (43) with the lumen for further deployment. The distal diameter (45) should not be appreciably smaller than the lumen diameter (44) lest the retaining device assembly (43) begin to block blood flow. We believe that the distal diameter (45) should be at least 75% of the lumen diameter (44).

It should also be noted that the proximal diameter portion of the retaining device assembly (43) does not completely cover the mouth (6) of the aneurysm (4) in the Figures. This is not critical but the is an option in this variation.

Figure 4C:
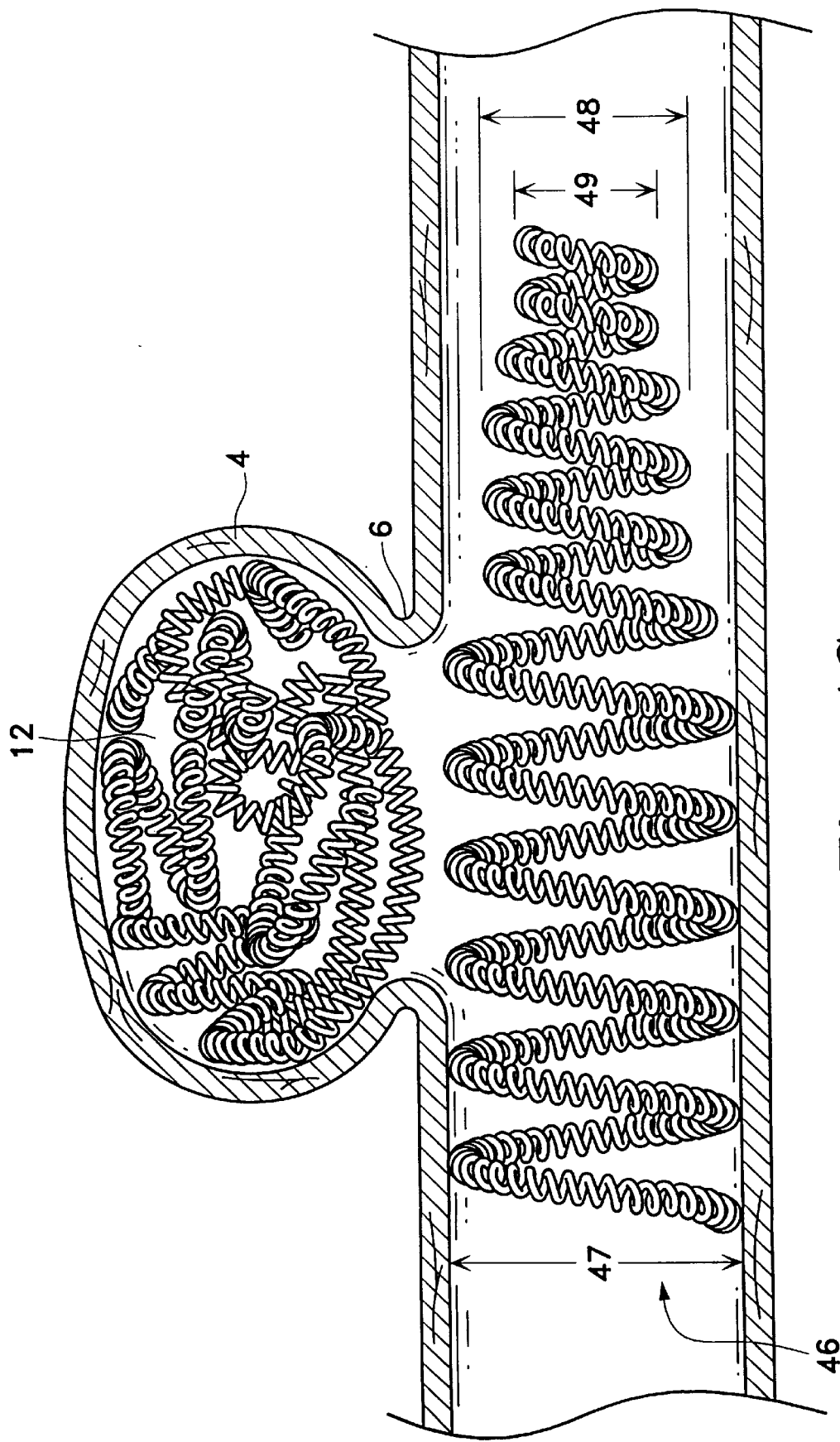

FIG. 4C shows a similar variation of the invention in which the distal portion of the retaining device assembly (46) is stepped and has two short sections of respectively smaller diameters (48,49).

Semi-Penetrable Retaining Device

A further artificial occlusion kit embodiment allows for implantation of the retaining device prior to implantation of occlusion devices, an embodiment particularly useful in "wide-neck" aneurysms. In artificially occluding these types of body spaces using conventional systems, occlusion devices may not be implantable at all into the aneurysm without immediate migration into a flowing vessel prior to insertion of a retaining device at the entrance zone. This embodiment solves this problem by providing semi-penetrable spaces in the retaining device at the entrance zone from the body lumen to the adjacent body space to be occluded.

Figure 5:
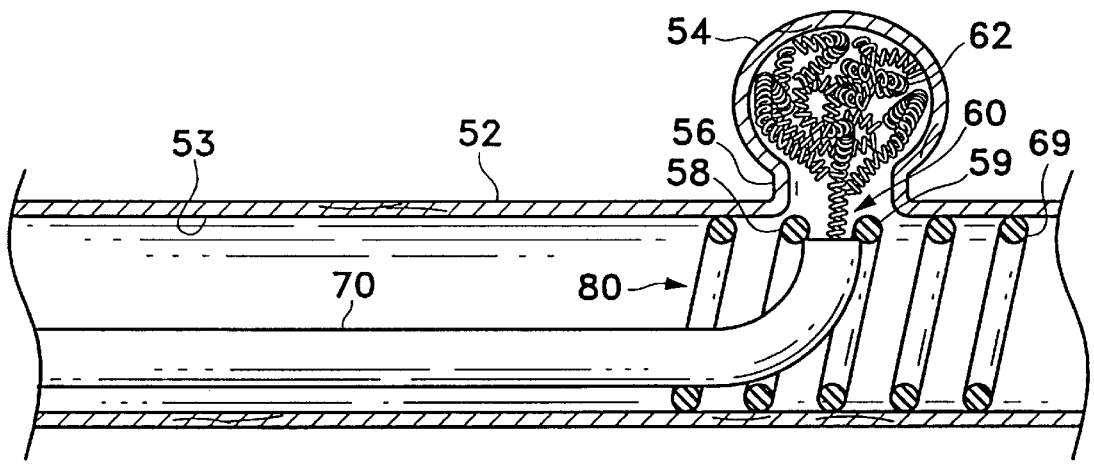
FIG. 5 shows a side view of a vessel having in its wall a wide-neck aneurysm, showing a variation of the artificial occlusion kit where the retaining device has a semi-penetrable space through which an artificial occlusion device is being introduced into an aneurysm.
Figure 6:
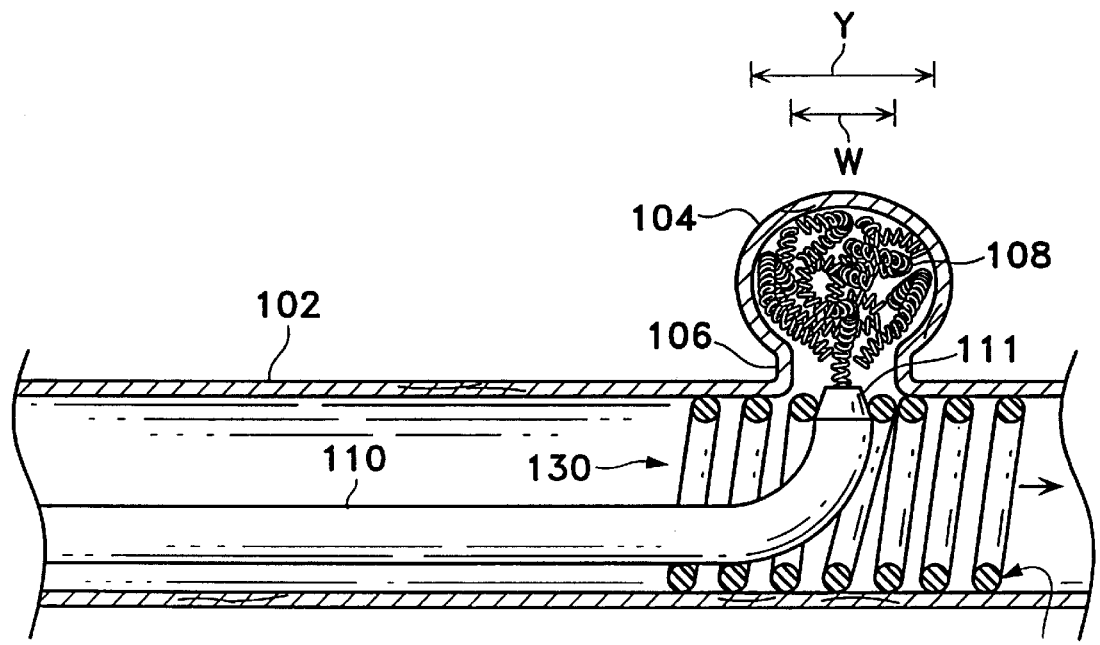
FIG. 6 shows a side view of a vessel having in its wall a wide-neck aneurysm, showing a variation of the artificial occlusion kit where the retaining device has a distensible semi-penetrable space that is shown distended by a delivery catheter through which vaso-occlusion coils are being introduced into the aneurysm.
Figure 7:
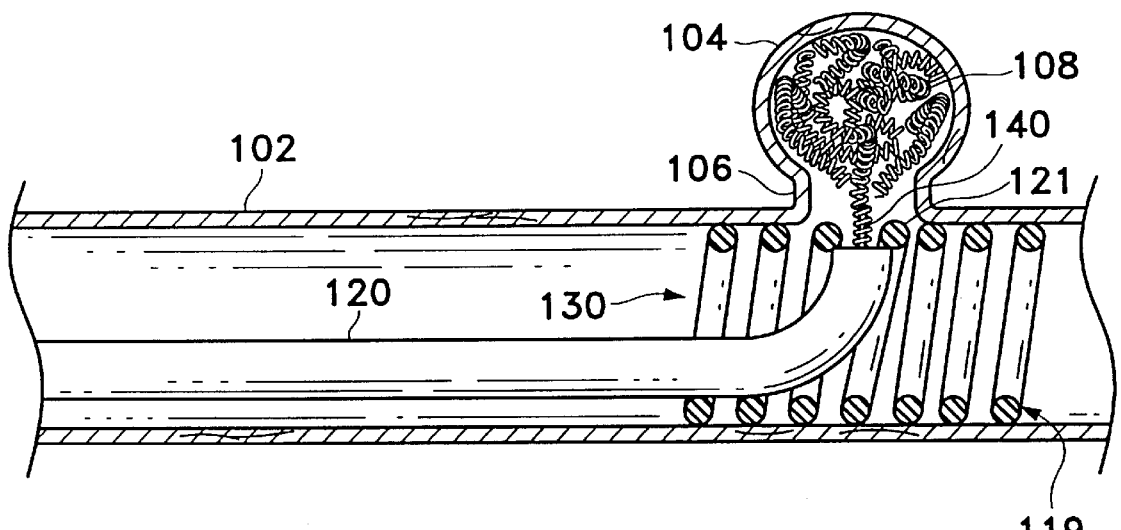
FIG. 7 shows a side view of the vessel and wide-neck aneurysm, showing a further variation of the assembly shown in FIG. 5, wherein the distensible semi-penetrable space is shown distended by an introducer wire over which vaso-occlusion coils are being coaxially advanced into the aneurysm.

As is shown in FIGS. 5–7, the retaining device in the variations of this embodiment may be a helically wound member, wherein the semi-penetrable space for occlusion device insertion is provided by the space between adjacent windings of the helix. In a preferred mode, the helically wound member that forms the retaining device is a metal wire wound into a primary helix which is further wound into a secondary helix. In this mode, windings of the secondary helix form the semi-penetrable space for occlusion device insertion.

In the variation shown in FIG. 5, the predetermined, semi-penetrable space (60) of retaining device (69) is defined by the space between adjacent helical windings (58) and (59). This semi-penetrable space (60) is equal to or greater in diameter than occlusion device (62) when it is being introduced into aneurysm (54). However, semi-penetrable space (60) is less than the diameter of occlusion device (62) after it is in the aneurysm. Thus, in this embodiment, the spacing provided by the retaining device allows the introduction of occlusion devices into the aneurysm but does not allow significant migration of occlusion devices, once implanted, back into the adjacent vessel lumen (53).

More particularly, in FIG. 5 the occlusion device (62) is radially constrained to a first shape having a first outer diameter when within the delivery lumen of delivery catheter (70). The delivery catheter distal end is abutting the inner surface of the retaining device (69). The occlusion device (62) is then advanced out the distal end of the delivery catheter (70) and through the space in the retaining device (69), where it is then radially artificially unconstrained. Once released into the aneurysm sac through the retaining device semi-penetrable space, the occlusion device (62) takes on a second shape having a second outer diameter that prevents it from migrating back through the semi-penetrable space and into the body lumen (53).

In a more particular embodiment of the artificial occlusion kit shown in FIG. 5, the semi-penetrable spaces of the retaining device are distensible. This distensibility enhances the semi-penetrability of the spaces. More specifically, occlusion devices may be introduced through such spaces when an applied force distends open the spaces. Once the occlusion devices are implanted into the occlusion site, however, passive migration of the devices back through the spaces does not provide the requisite force to distend open these spaces—the passive migration is thus prevented.

In one aspect of this variation, a particular occlusion device may be used in conjunction with a retaining device, and be of such construction and dimension that it may be advanced unaided through the spaces provided in the retaining device. For example, detachable occlusion devices such as those described in U.S. Pat. No. 5,122,136 or U.S. Pat. No. 5,354,295 may be constructed with sufficient pushability to be advanced between adjacent coil winds of the retaining device and into the aneurysm sac. They may thereafter be detached within the aneurysm for occlusion.

Another aspect of this variation is shown in FIG. 6. Here, retaining device (119) is shown implanted into vessel (102) such that it radially engages the vessel wall adjacent to entrance zone (106) to wide-neck aneurysm (104) and bridges across entrance zone (106). The helical shape of retaining device (119) is shown to have a pre-determined spacing which may be spread when adjacent helical windings are forced apart. In FIG. 6, delivery catheter (110) is advanced through the retaining device and into the entrance zone (106) of the aneurysm (104).

In the particular variation of FIG. 6, delivery catheter (110) has a tip (111) which is tapered and dimensioned such that adjacent helical windings of retaining device (119) are forced apart when delivery catheter (110) is forced radially against the retaining device (119) from its inner lumen (130) and toward the entrance zone (106). To achieve this interaction, delivery catheter (110) may, for example, have a pre-shaped bend in the distal delivery catheter region ending in tip (111). This shape may aid in the advancement of the delivery catheter through the branching vasculature, or may also be sufficiently straightened coaxially over a guidewire to avoid proximal vessel trauma while tracking to the site.

In a further variation shown in FIG. 7, an introducer wire (140) may be forced through spaces provided in the retaining device, such as between adjacent winds of a helically shaped retaining device as shown in FIG. 7. Once the introducer wire (140) is advanced through the retaining device and into the aneurysm, a delivery catheter such as delivery catheter (110) (shown in FIG. 6) may thereafter be advanced coaxially over the introducer wire (140) and into the entrance zone of the wide-neck aneurysm. An advantage to using an introducer wire in this technique as compared to that previously described in reference to FIG. 6 is that the delivery catheter may be introduced into the aneurysm over the introducer without the need for preshaping the delivery catheter.

In the particular variation of FIG. 7, however, delivery catheter (120) is not shown to be advanced into entrance zone (106) or aneurysm (104), but rather is advanced merely to abut the inner diameter of the helical windings forming retaining device (119). Vaso-occlusion coil (108) is shown being advanced coaxially over introducer wire (140) while advancing through delivery catheter (120), through adjacent windings of helical retaining device (119), and ultimately off the distal end of introducer wire (140) and into the sac of aneurysm (104). Such coaxial advancement of vaso-occlusion coil (108) may occur, for example, by coaxially advancing a pusher member, located proximally of vaso-occlusion coil (108), in the distal direction against a proximal end of vaso-occlusion coil.

The critical performance of the introducer wire is that it must be sufficiently stiff and of such diameter and geometry to allow it to pass through the spacing provided in the retaining device (119). However, it should also not be too stiff so as to present risk of trauma or perforation of the thinned aneurysm wall. Such introducer wire (140) may also be shapeable such that it is adapted for tracking to the retaining site adjacent the aneurysm, as well as for advancing through the spaces in the retaining device barrier at the aneurysm entrance zone. Conventional guidewires of the type known in the art may perform sufficiently as introducer wire (140) in a particular case. Alternatively, the present invention further contemplates obvious alterations to known wire designs in order to function with the individual features of a particular retaining device design, as may be apparent to one of ordinary skill. Such particularized retaining device features that may dictate introducer wire design parameters, for example, may be the diameter and degree of distensibility of the semi-permeable space.

"Coil Over Core" Retaining Device

Figure 8:
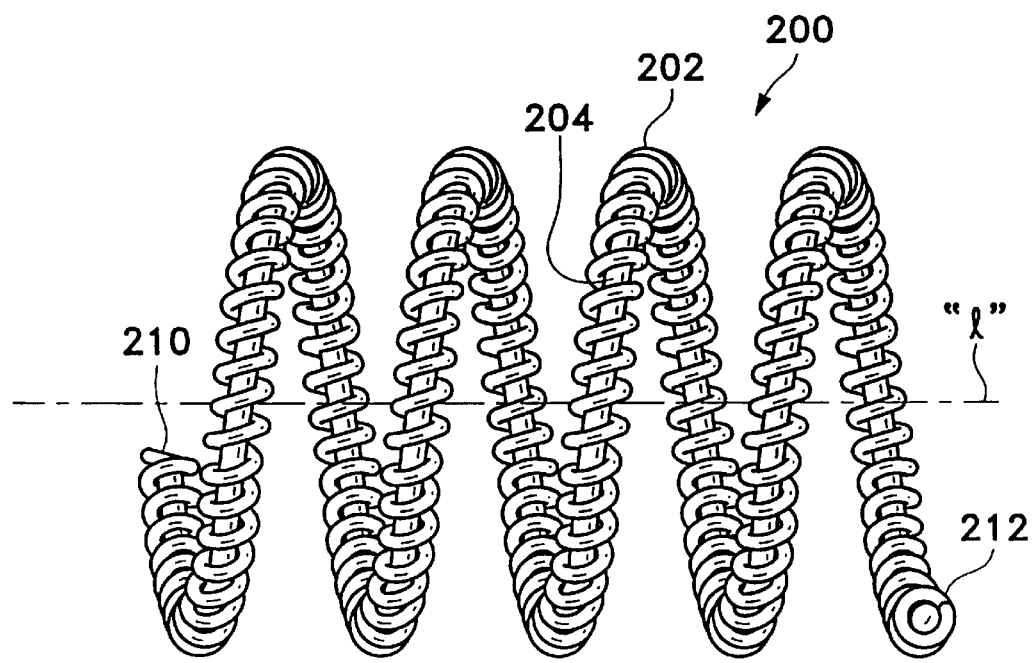
FIG. 8 shows a perspective view of a further variation of retaining device wherein the retaining device is shown to be constructed of a wire wound into a helix over a core member, the helical wire and core member being formed into a secondary geometry.
Figure 9A:
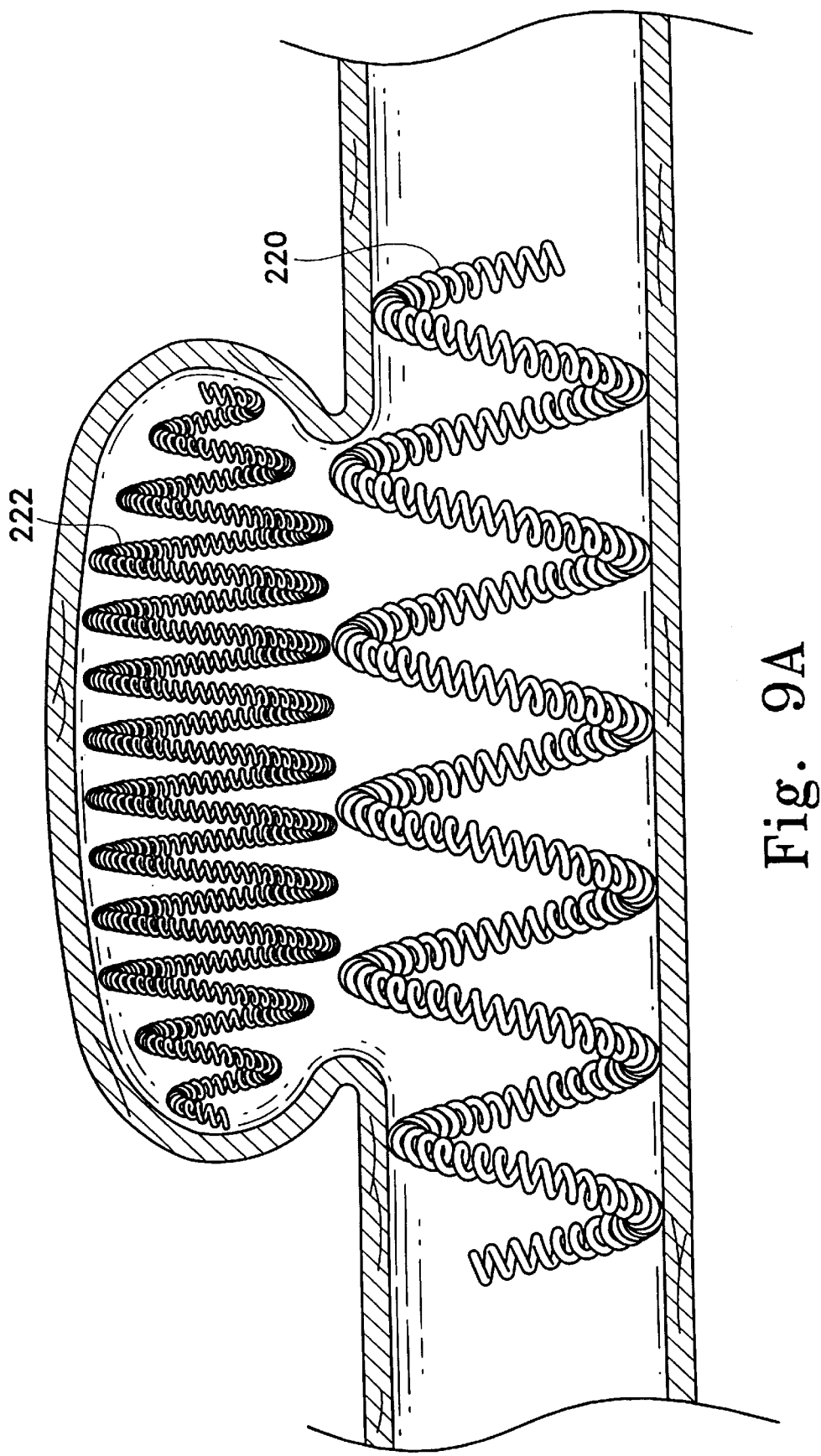
FIGS. 9A and 9B show in schematic cross-section anatomically shaped filler coils suitable for use in conjunction with the retention devices made according to this invention.
Figure 9B:
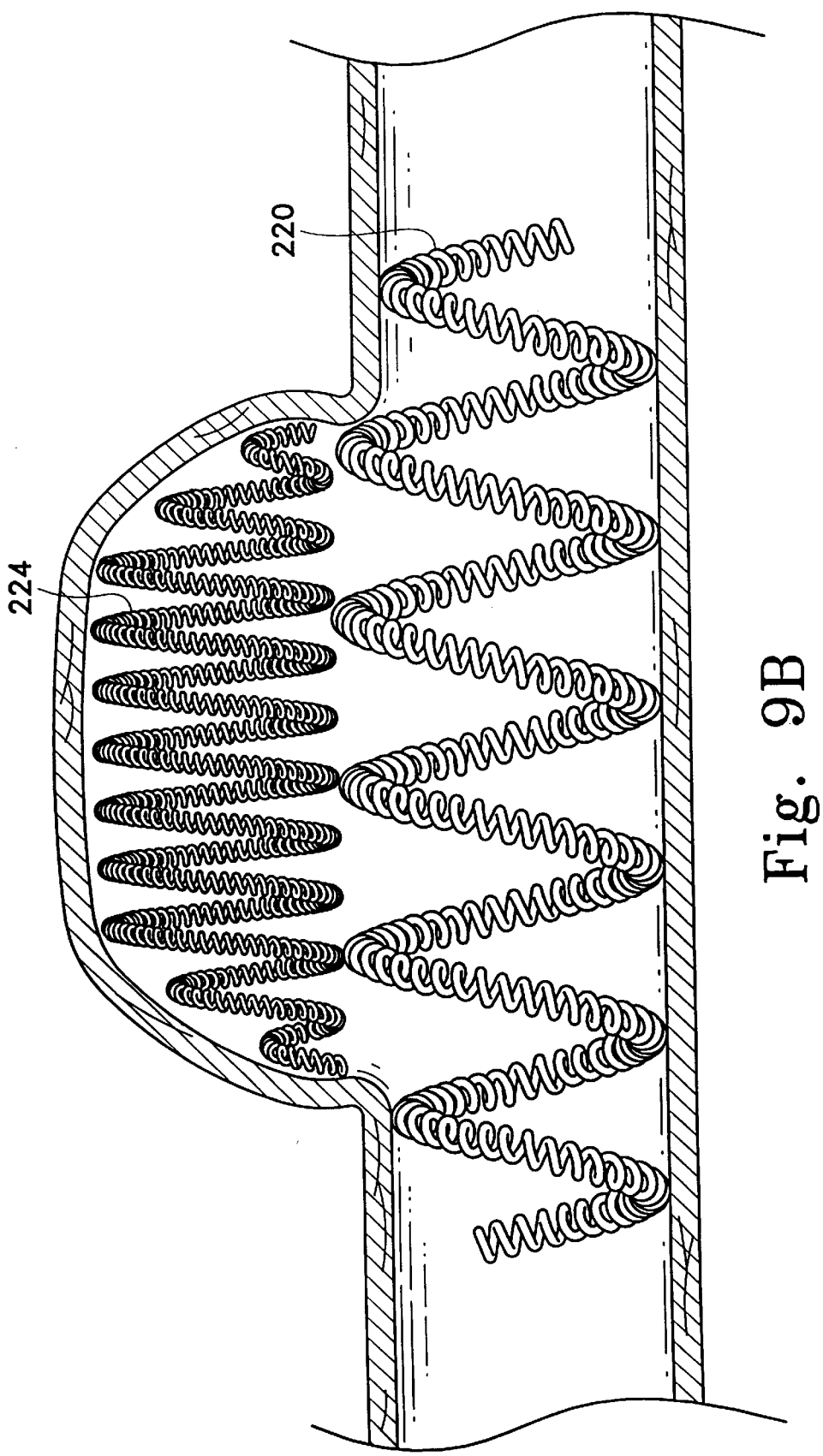

A further embodiment of the present invention is shown in FIG. 8. In this variation, the implantable medical device that functions as a retaining device in the novel artificial occlusion kit has a particular construction that includes a wire (202) wound into a primary helix over an inner core member (204). The inner core member (204) and primary wire helix are also wound into a secondary geometry, and are soldered or welded at both of two ends (210) and (212). The secured ends (210) and (212) serve to secure the "wire over core" composite relationship and also provide smooth ends for safety considerations in this implantable device.

Preferably, the inner core member (204) is a metal mandrel, and more preferably is a superelastic alloy of nickel-titanium. In one particular variation, the inner core member (204) is constructed of a nickel-titanium alloy and has an outer diameter from 0.003" to 0.006". The helically wound wire (202) in this preferred variation may be a radiopaque metal, such as platinum, gold, or tungsten, and has an outer diameter in the range of 0.001" to 0.006". The coil may have 0–100% spacing. Preferably, wire (202) is wound at a pitch of 0.001" to 0.008" with 0–100% spacing. For instance, a coil made with 0.003" wire with 0.006" pitch has 100% spacing; a coil with 0.003" wire and 0.006" pitch has 0% spacing.

In this variation, wire (202) is secured to the inner core member (204) using the following process: the coil is secured to the inner core member at least two or several locations, preferably at both ends. One method for joining the components involves resistance welding or a similar such process. Soldering or brazing is similarly useful in joining the metals.

In the "wire over core" combination structure such as that just described, the inner core member (204) is chosen such as to provide the requisite shape memory and stiffness. This inner core member may not by itself provide optimal radiopacity, since it is not chosen for that purpose. The requisite radiopacity of the device may instead be provided by the outer wound coil (202), which might not provide optimal stiffness or material memory if it were only available alone in the device. It is believed that the combined features of this "wire over core" design may optimally adapt prior known implantable coil technologies to meet the particular structural needs of a retaining device in the current invention.

For instance, it is important that the elongate retaining device be flexible along its length so that it can be implanted into lumens having bends. However, it is believed that too much flexibility may correspond to irregular and random conformations of the coil when implanted in-vivo, which may produce an occlusive effect. A primary helical coil wound into a secondary helix, without more, may be too flexible to effectively engage a vessel wall along the requisite length to form a barrier against occlusion device migration. However, the addition of the mandrel in what would otherwise be the primary helix lumen provides a stiffening structure that still allows for a certain controlled flexibility of the secondary helical shape.

Additionally, prior vaso-occlusion coils require substantial space filling for effective cross-sectional blockage of a body lumen, for example. In these devices, only a minimal portion of the device may be required to actually radially engage a vessel wall for primarily the purpose of anchoring the device at the occlusion site. This means only a small portion of the coil may need to reconfigure from a first constrained diameter during delivery to a second diameter at least approximating the lumenal wall diameter when delivered. It may be acceptable, even desirable, for such occlusion coils to have portions not so significantly altered in their cross-sectional diameter when they are delivered at an implantation site, so long as their shape presents an occlusion to flow.

In contrast, the present inventive retaining device must take on a shape at the retaining site that has sufficient outer diameter along a sufficient length of the device to form an effective barrier across the aneurysm entrance zone at the vessel wall. Impinging into the lumen's cross-section is generally undesirable. The reconfiguration to this expanded shape from a first radially constrained shape during delivery may correspond to a higher degree of requisite material memory than is possible from a simple fine wire wound into the primary and secondary helix shapes as previously disclosed. An inner core mandrel, however, may offer the structure necessary to provide such memory.

In another particular retaining device variation, the wire forming the primary helical core is wound much tighter than a similar wire might be wound to optimally form an occlusion device. It is believed that coil stiffness may be controlled by adjusting the outer diameter of the primary coil helix (e.g. tightness of winding) to which a given wire is wound. It is believed that, by providing one preferred retaining device may comprise a wire wound very tightly into a primary helix that has also a secondary shape.

One preferred application of this "tightly wound" variation comprises a platinum wire of 0.005" outer diameter wound over a 0.009" mandrel. In contrast, common known occlusion coils for occluding aneurysms is constructed a 0.005" wire wound over a 0.011" mandrel. Similarly, when a smaller diameter primary helix is desired, a wire having an outer diameter of 0.003" may be wound over a mandrel having an outer diameter of 0.007". In any case, the wire is thereafter annealed in the wound shape to form a primary coil of predetermined dimensions. A secondary shape may then be imparted to the primary coil, which secondary shape may also be a helical coil.

It should be apparent to those skilled in this art that the coil placed within an aneurysm need not be the random shape described and shown above. Indeed, many shapes would be suitable for use with this invention. We have found that anatomically shaped oval (222) or semi-oval (224) coils are suitable for this invention. It should be apparent that both these are regularly wound and are provided with the shape of the anatomical cavity into which they are placed. Coils (222) and (224) provide a similar amount a rate of occlusion within the aneurysm structure and yet do so with a significantly smaller mass of coil than the random shapes shown above in many of the drawings.

Other Clinical Applications and Design Embodiments

The ultimate goal of the particular artificial occlusion kits, novel components thereof, and related methods described above is to occlude aneurysms having entrance zones or necks that are of such width and geometry that conventional techniques would result in unwanted migration of occlusion devices from the aneurysm and into the adjacent vessel. However, the assemblies, components, and methods of the present invention that were conceived of in order to meet this need may provide additional benefits in other medical treatments. Additionally, the invention contemplates retaining device designs that meet the general requirements of the novel artificial occlusion kit but vary from the specific variations just described.

In one aspect of the invention, for example, the artificial occlusion kit embodiments and variations have been described specifically as applied to aneurysms in vessel walls. However, other occlusion sites adjacent to and in fluid communication with body lumens may present similar concerns as to migration of occlusion devices from an occlusion site and into an adjacent lumen. For instance, a vessel that branches off of a feeding vessel may be a body space to be occluded and the feeding vessel at a region adjacent to the branching vessel may be a desired retaining site. The present invention contemplates use of the apparatus embodiments described in such body spaces and lumens in addition to aneurysm sites in vessels.

The invention also broadly contemplates a retaining device structure that is expandable at a retaining site of a body lumen to form a barrier against migration of at least one occlusion device through an entrance zone between an occlusion site and an adjacent lumen, and that also provides a lumen for flow through the body lumen at the retaining site. Examples have been provided in the form of shape memory coils delivered through radially confining delivery sheaths or over delivery wires, in addition to an alternative balloon expandable retaining device embodiment. Various specific retaining device designs that meet the broad requirements provided, beyond the particular variations provided, are within the scope of this invention.

Also, while various retaining device designs may meet the requirements of the novel artificial occlusion kit described, at least one novel electrolytically detachable implantable medical device has been conceived of for use as a retaining device in the artificial occlusion kit. This novel implantable medical device may have useful medical applications in addition to retaining artificial occlusion devices. The scope of this aspect of the invention, while intimately pertaining to an artificial occlusion kit, should not be limited to the kit embodiments described for artificial occlusion.

Modification of the above-described variations for carrying out the invention that would be apparent to those of skill in the fields of medical device design are intended to be within the scope of the following claims.

We claim as our invention:

1. An implantable medical device assembly for engaging a body space wall in a mammalian body, comprising:

an elongate implantable member having two opposite ends, and wherein said member forms a first shape having a longitudinal axis and a first outer diameter on a radial aspect of said longitudinal axis when radially artificially constrained for percutaneous delivery into a body space having a body space wall, and a second shape about said longitudinal axis upon release from said radial constraint, said second shape having a second outer diameter larger than said first outer diameter and sufficient to engage the body space wall, and forming a lumen along said longitudinal axis with a lumen diameter sufficient to allow fluid flow through said implantable member wherein said second shape has at least one region having a reduced diameter.

2. The implantable medical device assembly of claim 1, further comprising a delivery catheter having a proximal end with a proximal delivery port, an opposite distal end with a distal delivery port, and a delivery lumen extending between said delivery ports and having a delivery lumen inner diameter less than said second outer diameter, wherein said elongate implantable member is slideably disposable under radial constraint within said delivery lumen.

3. An implantable medical device assembly for engaging a body space wall in a mammalian body, comprising:

an elongate implantable member having two opposite ends, and wherein said member forms a first shape having a longitudinal axis and a first outer diameter on a radial aspect of said longitudinal axis when radially artificially constrained for percutaneous delivery into a body space having a body space wall, and a second shape about said longitudinal axis upon release from said radial constraint, said second shape having a second outer diameter larger than said first outer diameter and sufficient to engage the body space wall, and forming a lumen along said longitudinal axis with a lumen diameter sufficient to allow fluid flow through said implantable member; and a power source electrically coupled to an electrolytically severable joint located at one of said opposite ends; and an electrode electrically coupled to said power source;

wherein a circuit may be formed when said electrode and electrolytically severable joint are both in contact with a patient.

4. The implantable medical device assembly of claim 3, wherein said power source comprises a direct current source.

5. The implantable medical device assembly of claim 4, wherein said power source comprises an alternating current source.

6. The implantable medical device assembly of claim 5, wherein said power source produces a signal comprising an alternating current signal superimposed over a direct current signal, said assembly further comprising a sensing circuit for monitoring changes in said alternating current signal indicative of progression of electrolytic detachment of said implantable member from an elongate pusher at said electrolytically severable joint.

7. An implantable medical device assembly for engaging a body space wall in a mammalian body, comprising:

an elongate implantable member having two opposite ends, and wherein said member forms a first shape having a longitudinal axis and a first outer diameter on a radial aspect of said longitudinal axis when radially artificially constrained for percutaneous delivery into a body space having a body space wall, and a second shape about said longitudinal axis upon release from said radial constraint, said second shape having a second outer diameter larger than said first outer diameter and sufficient to engage the body space wall, and forming a lumen along said longitudinal axis with a lumen diameter sufficient to allow fluid flow through said implantable member wherein said implantable member comprises at least one wire wound into a primary helix and having a secondary geometry imparted thereto and wherein said primary helix forms a primary helix lumen, said implantable member further comprising an elongate core member coaxially disposed within said primary helix lumen.

8. The implantable medical device assembly of claim 7, wherein said elongate core member is a metal.

9. The implantable medical device assembly of claim 8, wherein said metal is a super-elastic alloy.

10. The implantable medical device assembly of claim 9, wherein said super-elastic alloy comprises nickel and titanium.

11. The implantable medical device assembly of claim 1 wherein said elongate implantable member having two opposite ends further comprises a distal end having a distal diameter smaller than said body lumen and said second outer diameter.

* * * * *